Figure 1:
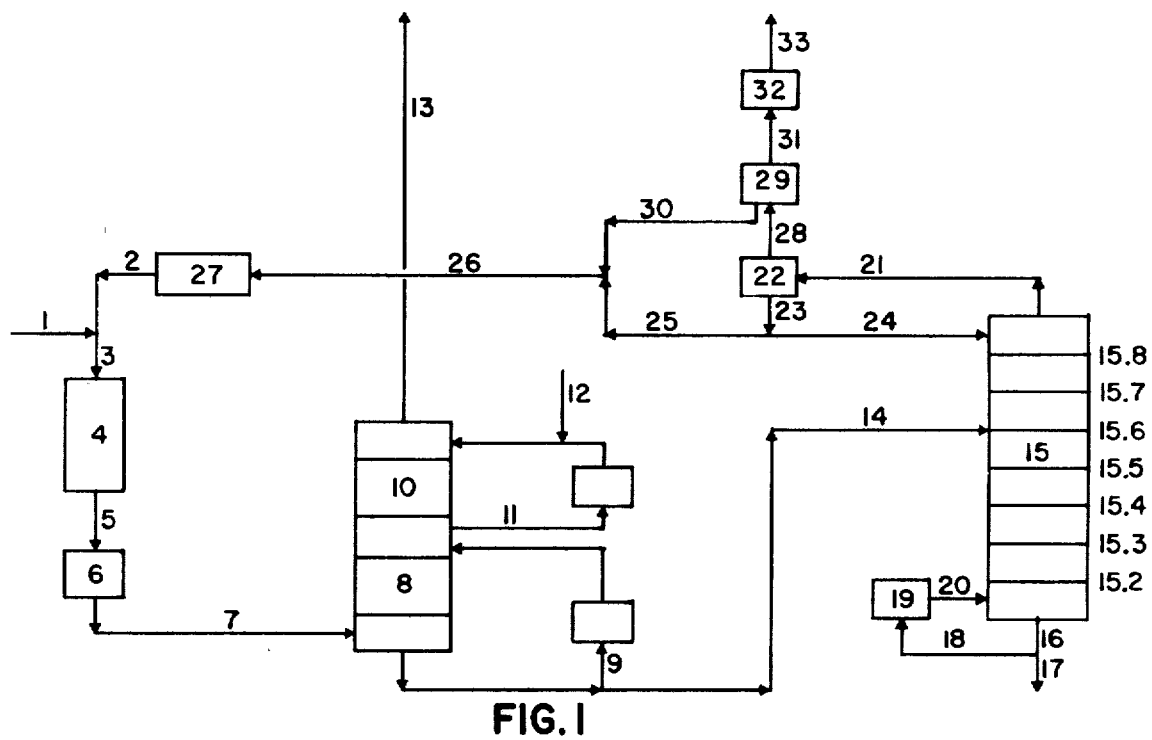

United States Patent [19]

Ferris et al.

[11] 4,454,354

[45] * Jun. 12, 1984

[54] MANUFACTURE OF AQUEOUS FORMALDEHYDE

[75] Inventors: Theodore V. Ferris; Richard C. Kmetz, both of Longmeadow, Mass.

[73] Assignee: Monsanto Company, St. Louis, Mo.

[*] Notice: The portion of the term of this patent subsequent to Sep. 7, 1999 has been disclaimed.

[21] Appl. No.: 404,210

[22] Filed: Aug. 2, 1982

[51] Int. Cl.³ .................... C07C 45/29; C07C 47/04
[52] U.S. Cl. ..................................... 568/473; 568/472
[58] Field of Search ........................... 568/473, 472

[56] References Cited

U.S. PATENT DOCUMENTS

| | | | |
|---|---|---|---|
| 3,113,972 | 12/1959 | Kodama et al. | 568/473 |
| 3,174,911 | 3/1965 | Webb et al. | 568/473 |
| 3,214,891 | 11/1965 | Kloepper et al. | 568/473 |
| 4,119,673 | 10/1978 | Aicher et al. | 568/473 |
| 4,343,954 | 8/1978 | Hoene | 568/473 |
| 4,348,540 | 9/1982 | Ferris et al. | 568/472 |

Primary Examiner—Werren B. Lone
Attorney, Agent, or Firm—R. Bruce Blance; William J. Farrington; Paul D. Matukaitis

[57] ABSTRACT

Formaldehyde manufacture by oxidative-dehydrogenation of methanol over a silver or copper catalyst. Aqueous formaldehyde solution is obtained from the reaction and is stripped of a mixture of methanol, formaldehyde and water by a low energy process at relatively low temperature and low reflux in a still comprising at least about 1.5 theoretical plates, the stripping conditions being selected to allow substantial reduction of the methanol content of the aqueous formaldehyde solution and recycle of the methanol to the reactor.

19 Claims, 2 Drawing Figures

MANUFACTURE OF AQUEOUS FORMALDEHYDE

BACKGROUND OF THE INVENTION

This invention relates to a process for the manufacture of formaldehyde by the oxidative dehydrogenation of methanol in the presence of a silver catalyst. More particularly this invention relates to a process for the manufacture of formaldehyde by the oxidative dehydrogenation of methanol in the presence of a silver or copper catalyst in which the aqueous formaldehyde product is stripped of methanol and water by distillation at about atmospheric pressure or under reduced pressure and at low reflux in a still which comprises a sufficient number of theoretical plates to allow substantial reversal of the methyl hemiformal reaction and substantial stripping of the methanol.

In the industrial manufacture of formaldehyde from methanol by dehydrogenating oxidation with air over silver or copper catalyst in the presence of steam, generally in a ratio of from 0.1 to 1.8 moles of water per mole of methanol, the formaldehyde is usually washed out of or scrubbed from the reaction gas with water. On absorption of the reaction mixture, the steam produced by the reaction and the steam and methanol left from the starting mixture are condensed. The formaldehyde combines with water to give methylene glycol and higher polyoxymethylene glycols and with residual methanol to give methyl hemiformal and polyoxymethylene glycol monomethyl ethers. The higher polyoxymethylene glycols tend to precipitate from concentrated aqueous formaldehyde solutions as paraform. Hence aqueous formaldehyde has been conveniently used at a concentration of about 30 to about 37% by weight since such solutions are stable over extended periods of time without precipitation of paraformaldehyde and have been conveniently used in the manufacture of phenolic and amino resins.

In more recent times, with the development of improved stabilizers to suppress paraformaldehyde formation, higher concentrations of aqueous formaldehyde have been accepted for the handling of formaldehyde and the manufacture of resins, and have provided energy savings since they improve shipping and handling efficiency and reduce the amount of water to be removed during the resin product preparation. Such concentrated solutions are generally prepared by distilling the aqueous formaldehyde solutions formed in absorbers at substantially atmospheric pressure under conditions which allow most of the unconverted methanol to be removed. The distillation step requires high reflux ratios and considerable energy input.

The present invention is an improved process for the preparation of aqueous formaldehyde solutions in which substantial amounts of methanol and water are removed from the aqueous formaldehyde solution formed in the absorber, by distilling the solution at about atmospheric or under reduced pressure in a still comprising at least about 1.5 theoretical plates. In contrast with the high reflux ratios conventionally used in the removal of methanol by distillation at atmospheric pressure, little or no reflux is used and considerable improvement in energy efficiency of the process is realized. By means of the distillation, a concentrated aqueous formaldehyde solution of low methanol content can be readily obtained and can be used advantageously in the manufacture of phenolic and amino resins. Methanol contents of less than 2 weight percent are readily obtained.

In summary, the invention is a process for the manufacture of an aqueous solution of formaldehyde comprising the steps of:

(a) oxidatively dehydrogenating methanol with air in the presence of a silver or copper catalyst and steam at elevated temperature;

(b) absorbing the reaction product in an absorption train comprising one or more absorption stages in series to form an aqueous formaldehyde solution containing free and combined methanol; and (c) distilling at low reflux a substantial fraction of the methanol from the aqueous formaldehyde solution in a distillation column comprising at least about 1.5 theoretical plates for methanol distillation, the still pressure at the top of the column being in the range of about 10 to 105 kPa.

Essentially the process is advantageously carried out continuously in the following sequence:

1. a mixture of water and methanol vapors is mixed with air, the mixture is passed over a silver or copper catalyst bed and the methanol is oxidatively dehydrogenated;

2. the reaction product comprising a gaseous mixture of formaldehyde, steam, residual methanol, nitrogen, carbon dioxide and hydrogen is cooled and fed to an absorber comprising a series of stages containing aqueous formaldehyde solution, each stage being equipped with a scrubbing and cooling system. Sufficient water or dilute aqueous formaldehyde solution is added to the final absorber stage to maintain the desired concentration of formaldehyde in the final product, and aqueous formaldehyde solution is passed through the absorber countercurrently to the reaction gas mixture to absorb most of the formaldehyde, water and methanol from the gas mixture. The off-gas from the absorber comprising nitrogen, some carbon monoxide, carbon dioxide and hydrogen, and minor amounts of water, methanol and formaldehyde issues from the top of the absorber and can be burned for its fuel value;

3. aqueous formaldehyde solution is fed from the absorber to a distillation column comprising at least about 1.5 theoretical plates, operated at a pressure in the range of about 10 to about 105 kPa at the top of the column;

4. at least a part of the vapor stream is recycled to the initial reaction mixture comprising water and methanol and the remainder is returned to the top of the still column as reflux, the reflux ratio being about 5 or less;

5. the aqueous formaldehyde solution which is drawn from the bottom of the distillation column constitutes the final formalin product from the process.

In general the absorber can contain any number of absorption or scrubber stages for absorption of the reaction products of the oxidative dehydrogenation of methanol. Conveniently from 2 to 4 absorption stages each equipped with a scrubbing and cooling system may be used. Sufficient water is continuously added to the system to maintain the desired formalin product concentration, and the temperatures and concentrations of the aqueous formaldehyde solutions in the stages are preferably maintained at levels for effecient absorption of formaldehyde and methanol from the reaction gas stream without formation of paraform in the stages. Part of the absorbing stream from at least the first absorption stage is passed to the distillation column. Preferably none of the aqueous formaldehyde solution passed to the distillation column from the first absorption stage is returned directly to the absorber. It is preferably taken off at the bottom of the stripping column as formalin product. Optionally part of the absorbing stream from at least the first two absorption stages can be passed to the still column, the points of entry being intermediate to top and bottom of the still column with the more dilute aqueous formaldehyde solution entering near the top and the more concentrated aqueous formaldehyde solution entering near the bottom while at the same time the more dilute aqueous formaldehyde solution after descent in the distillation column may be partly drawn off as a side stream above the entry point for the more concentrated solution and added to the absorption stream of the prior more concentrated aqueous formaldehyde absorption stage to maintain the concentration of formaldehyde in that absorption stage at a level to avoid formation of paraform at the particular temperature of the stage. Where part of the aqueous formaldehyde solution in an absorption stage other than the first absorption stage is supplied to the distillation column the side stream from the distillation column may provide the only route whereby formaldehyde solution from that absorption stage can flow to the prior absorption stage containing more concentrated aqueous formaldehyde. The distillation column can have as many entering streams as there are absorption stages in the absorber, the streams providing a formaldehyde concentration gradient in the distillation column.

The operation of the distillation column is dependent on several variables including the temperature of the column, the pressure of the column, the reflux ratio, the number of ideal stages or theoretical plates in the column, the residence time of the aqueous formaldehyde solution and the number and the composition of aqueous formaldehyde streams supplied to the column from the absorber.

The temperature and pressure of the column are directly dependent variables. Therefore the temperature required to cause the aqueous formaldehyde solution to boil will be high if the selected column pressure is high and will be low if the column pressure is low. Since the column is operated under steady state conditions at flow rates of liquid and vapor which allow efficient distillation without entrainment of the liquid in the vapor stream, pressure and temperature will increase from top to bottom of the column, the increase being dependent on the number of theoretical plates in the column.

Advantageously the pressure at the top of the column is less than about 50 kPa and is preferably less than about 35 kPa to provide a column temperature at which the volatility of methanol relative to formaldehyde enhances the ratio of methanol to aqueous formaldehyde in the vapor stream emerging from the distillation column and improves the efficiency of methanol stripping. The pressure at the top of the column is advantageously maintained at least at about 10 kPa so that the vapor density is sufficiently high to avoid the need for an excessively wide distillation column to obtain efficient distillation stripping of commercial quantities of aqueous formaldehyde solution. Preferably the pressure at the top of the column is in the range of about 20 to about 35 kPa and the temperature is in the range of about 60° to about 85° C., to allow the vapors to be condensed readily and returned in part as a reflux to the distillation column. The reflux ratio is advantageously about 5 or less and is preferably about 2.5 or less.

In order to obtain significant removal of methanol from the aqueous formaldehyde by means of the distillation column without excessive removal of formaldehyde, the distillation column should comprise at least about 1.5 theoretical plates and preferably about 3 or more theoretical plates. The number of theoretical plates is determined from the following relationship:

$$NTP = \frac{P_t - P_b}{\frac{1}{2}(\Delta P_t + \Delta P_b)}$$

where
NTP = number of theoretical plates in the distillation column under steady state conditions,
$P_t$ = vapor pressure of methanol in the vapor stream emerging from the top of the distillation column,
$P_b$ = vapor pressure of methanol in the vapor stream at the bottom of the distillation column,
$\Delta P_t = P_t(e) - P_t$
$P_t(e)$ = equilibrium vapor pressure of methanol for the aqueous formaldehyde/methanol solution at the top of the column, at the temperature at the top of the column,
$\Delta P_b = P_b(e) - P_b$
$P_b(e)$ = equilibrium vapor pressure of methanol for the aqueous formaldehyde/methanol solution at the bottom of the column, at the temperature at the bottom of the column.

The equilibrium vapor pressures are determined from standard vapor liquid equilibrium data, for example they may be obtained from data stored in the data base sold by Monsanto under the registered trademark Flowtran.

In aqueous formaldehyde solutions a methanol-methyl hemiformal-polyoxymethylene glycol monomethyl ether equilibrium exists and favors the hemiformal and monoethyl ethers derived therefrom. The equilibrium can be displaced towards methanol by raising the temperature and by dilution of the formaldehyde solution with water. Methanol can be readily removed from dilute aqueous formaldehyde solutions by fractional distillation. However, with concentrated solutions of aqueous formaldehyde which are gaining commercial favor, wherein the formaldehyde concentration is above about 40 weight percent and particularly wherein the formaldehyde concentration is above about 50 weight percent, processes to remove methanol and in particular the distillation process of the present invention to remove methanol at the relatively low temperatures used with the purpose of conserving energy, is more difficult because most of the methanol is chemically combined as hemiformal or monomethyl ethers at these temperatures. Although reversal to methanol occurs progressively with the removal of methanol from the solutions, the rate of reversal is rather low. Efficient removal of methanol in a distillation column comprising conventional packing or tray columns would require an excessively high column. It is therefore advantageous to increase the residence time of the aqueous formaldehyde in the stripping column by any convenient means to allow reversal of the reactions which tie up the methanol. Preferably residence zones are introduced to allow the aqueous formaldehyde solution to reside in the column for at least about 20 minutes. The column then becomes a series of stripping zones separated by residence zones, with the free methanol being generated by reversal of the methanol hemiformal reaction in the residence zones. One way to obtain residence zones is by introduction into the column of a number of chimney trays which are essentially overflow liquid trays with gas chimneys to allow the ascending vapors to pass by the aqueous formaldehyde solution held in the chimney trays. Another way is by means of circulation loops placed at intervals along the distillation column, the loops being equipped with reservoirs of suitable size to isolate the formaldehyde solution from the vapor stream for the desired time. Thus with distillation columns comprising conventional packing or trays such as sieve trays, glass trays, bubblecap trays or valve trays to provide intimate contact between the aqueous formaldehyde solution and the vapor for efficient separation of methanol by the vapor stream, it is advantageous to include resistance zones at intervals in the column to reduce the height of the column required for efficient stripping of methanol. For example a 30 meter distillation column capable of handling about 5 metric tons of formalin product per hour, provides about four theoretical plates for the stripping of methanol determined by means of the relationship set forth above, when it is packed with 21 meters of Pall ring packing divided into 5 zones with each zone separated with a chimney tray of 10 cm. depth, providing a residence time of about 6 minutes in each residence tray. Similarly a 30 meter still column containing 45 sieve trays can provide about four to about seven theoretical plates when 4 residence trays each providing a residence time of about 6 minutes are placed at intervals along the column. Thus by means of the residence zones, theoretical plates of height in the range of about 0.5 to about 10 meters are readily obtained and allow the weights of vapor and liquid passing through the distillation column per unit time to be of about the same order of magnitude. Preferably the weight ratio is in the range of 0.3 to about 1.5.

The vapors which emerge from the distillation column comprising methanol, formaldehyde and water also entrain minor amounts of nitrogen, hydrogen and carbon dioxide carried over from the absorption train. Depending on the initial concentration of methanol in the aqueous formaldehyde solution and the operating conditions of the distillation column, the vapors can be richer in methanol by as much as twenty times the concentration of methanol in the aqueous formaldehyde solution supplied to the column from the absorption train. At the same time some increase in the water concentration is obtained in the vapors compared with the aqueous formaldehyde solution fed to the column. As a result the aqueous formaldehyde solution obtained as product at the still bottom is enhanced in formaldehyde concentration and is considerably reduced in methanol concentration.

Advantageously, the vapors emerging from the top of the distillation column can be fed directly to the vaporized reaction mixture of methanol and water with suitable adjustment to maintain the desired ratio of methanol and water in the reaction mixture. Such direct recycle is especially advantageous when the concentration of methanol in the aqueous formaldehyde solution fed from the absorption train to the distillation column is already quite low, for example less than about 4 weight percent. However, when the concentration of methanol in the aqueous formaldehyde solution fed from the absorption train to the distillation column is greater than about 4 weight percent, recycle of all the vapors emerging from the distillation column to the converter may be undesirable because such recycle would generate a rather high concentration of formaldehyde in the reaction mixture and would tend to harm the reactor time/space relationship and increase the thermal energy used in distillate recycle vaporization. Optionally therefore the vapors issuing from the top of the distillation column may be passed to a reflux condensor to condense an aqueous formaldehyde solution which is rich in methanol. Part of the condensate can be returned to the distillation column to increase the efficiency of the stripping process and part can be vaporized and recycled to the converter. Advantageously the ratio of refluxed to recycled condensate is selected so that the mole ratio of recycled formaldehyde to total methanol fed to the reactor is less than about 0.035.

Because a major portion of the methanol present in the aqueous formaldehyde solution fed to the distillation column can be advantageously removed by the stripping action, the aqueous formaldehyde-methanol solution recycled to the reactor is characterized by a methanol to formaldehyde mol ratio of at least about 0.6, and a ratio of at least about 1.0 can be readily achieved. This mol ratio is generally at least about 10 times higher than the ratio of the solution fed to the column from the first absorption stage of the absorber.

In comparison with a rectifying distillation column operated at ⅛ to one atmosphere pressure for removal of almost pure methanol from the aqueous formaldehyde solution produced in the absorber, the stripping process of the present invention can reduce the energy requirement for methanol removal by about 50 percent or more without significant sacrifice in separating efficiency.

Since the distillation column, and particularly the lower stages of the column, is operated in the present invention at relatively low temperatures in comparison with a usual rectifying distillation column, and since the reflux returned to the distillation column is a minor fraction of the total amount of aqueous formaldehyde solution in the column, heat required to maintain the column at the operating temperature can be readily supplied by the absorption solution from the first stage of the absorber optionally supplemented by a small reboiler unit at the bottom of the column.

Figure 2:
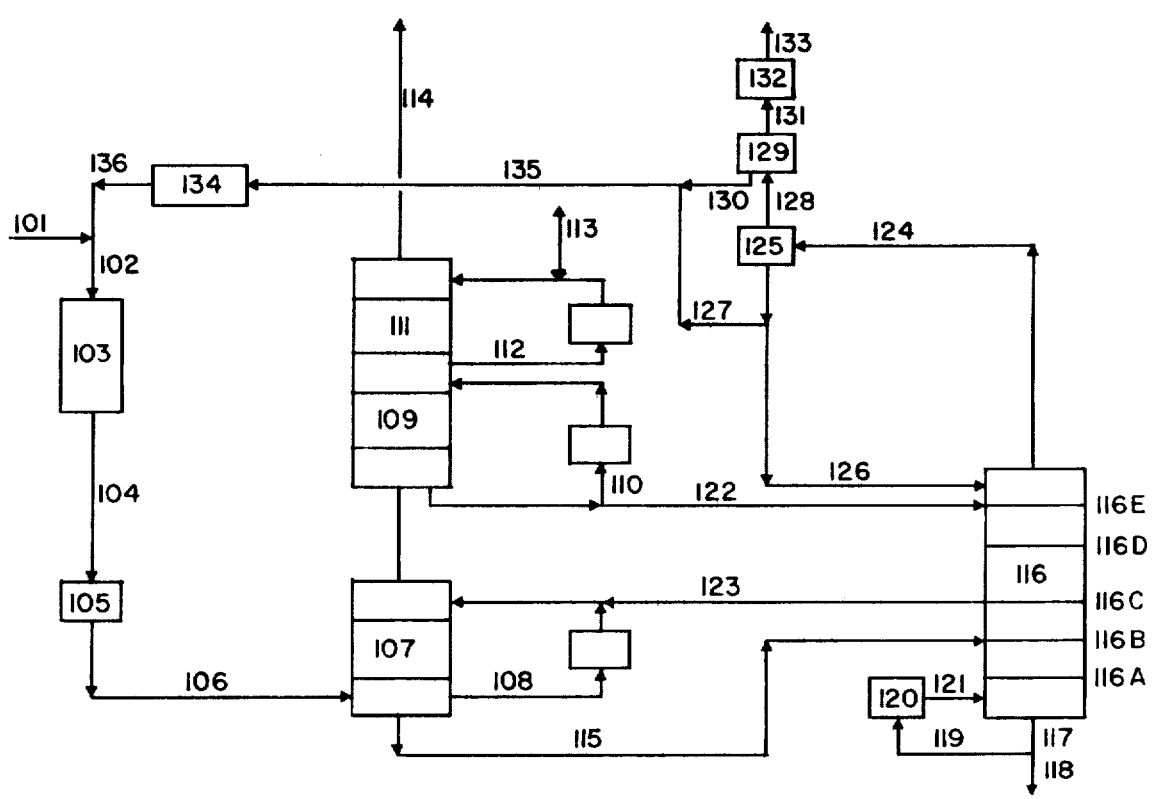

FIGS. 1 and 2 are diagramatic representation of the process of manufacture of ageous formaldehyde.

The process may be carried out by the following method A (FIG. I): Air, methanol vapor and water vapor are charged continuously through an inlet 1 and fed via line 3 into a reactor 4 equipped with a silver catalyst bed. After reaction in 4, the reaction mixture passes via connecting line 5 to a waste heat boiler 6 then via connecting line 7 into a two stage absorber. The two stages of the absorber, 8 and 10 are equipped with circulation loops 9 and 11. Water is fed to the absorber through line 12 and the off-gas comprising nitrogen, carbon dioxide, hydrogen and minor amounts of water, methanol and formaldehyde is removed from the system via line 13 to a furnace where the off-gas may be utilized for its fuel value. The aqueous formaldehyde solution formed in the first stage of the absorber is passed via line 14 to the fifth stage of a seven stage distillation column 15 operated at subatmospheric pressure. The liquid from the bottom of the distillation column passes through line 16. Most of the liquid is taken off through line 17 and passed to storage. The remainder is passed to a reboiler 19 via line 18 and vapors from the reboiler via line 20 back to the first stage of the distillation column. The vapors which emerge via line 21 from the top of the distillation column are passed to a reflux condenser 22 and the condensate is passed via line 23 to a three-way location. Part of the condensate is returned via line 24 to the top of the distillation column, part is passed via line 25 to a three way location where it is united with the condensate of a vent condenser 29 via line 30. The vent condenser 29 is connected with the reflux condenser 22 via line 28. The non-condensible gas which emerges from the vent condenser 29 via line 31 passes through a vacuum pump 32 and to the atmosphere via line 33. The combined condensate of lines 25 and 30 is passed via line 26 to a vaporizer 27 and the vaporized condensate is added to the reaction mixture via line 2.

Alternatively the process may be carried out by method B (FIG. 2): air and water and methanol vapor through line 101 are combined with a recirculated vaporized mixture of water, methanol and formaldehyde added via line 136 and charged continuously via line 102 to a reactor 103. After reaction in 103, the reaction mixture passes via connecting line 104 into a waste heat boiler 105 and thence via line 106 to a three-stage absorber consisting of stages 107, 109 and 111 with recirculation loops 108, 110 and 112 respectively. Water is added to the absorber via line 113 and off-gas is removed via line 114. Part of the absorption product of stages 107 and 109 is removed from the circulation loops and delivered to the distillation column 116 via 115 and 122 respectively. Line 115 enters the distillation column about half-way up the column and line 122 nearer the top. A major portion of the product is removed from the bottom of the column via lines 117 and 118, the rest being recirculated via lines 119 and 121 via reboiler 120. A side stream from the column is taken off via line 123 at a point above the entry of line 115 and is added to recirculation loop 108 of the first stage 107 of the absorber. The vapors which emerge via line 124 from the top of the distillation column are passed to a reflux condenser 125. Part of the condensate is returned via line 126 to the top of the distillation column, part is passed via line 127 to a three way point where it is united with the condensate of a vent condenser 129 via line 130. The vent condenser 129 is connected with the reflux condenser 125 via line 128. The non-condensible gas which emerges from the vent condenser 129 via line 131 passes through a vacuum pump 132 and to the atmosphere via line 133. The combined condensate of lines 127 and 130 is passed via line 135 to a vaporizer 134 and the vaporized condensate is added to the reaction mixture via line 136.

In the embodiments of the invention, the absorber comprises at least two stages or columns. In the first stage or column, the aqueous formaldehyde solution preferably contains from about 45 to about 70 weight percent of formaldehyde, from about 1.0 to about 6 weight percent methanol and from about 25 to about 54 weight percent of water; in the second stage, the aqueous formaldehyde preferably contains from about 20 to about 45 weight percent formaldehyde, from about 2.5 to about 7.5 weight percent of methanol and from about 47.5 to about 77.5 weight percent water; and in the third stage, the aqueous formaldehyde preferably contains from about 5 to about 20 weight percent formaldehyde, from about 4 to about 15 weight percent methanol and from about 65 to about 91 weight percent water. The absorption is preferably carried out at temperatures in the range of about 55° to about 90° C. in the first absorption stage, about 20° to about 60° C. in the second stage and about 10° to about 35° C. in the third stage. Advantageously the aqueous formaldehyde solution supplied to the distillation column from the second absorption stage and optionally from succeeding absorption stages may be heated prior to entry into the stripping column to about the temperature maintained at the entry point under steady state conditions of operation of the column.

The formaldehyde solution manufactured by the process of the invention, is a disinfectant, tanning agent, reducing agent and a starting material for the manufacture of organic chemicals and synthetic resins and adhesives.

The invention is further illustrated but is not intended to be limited by the following examples in which parts and percentages are by weight unless specified otherwise.

EXAMPLE 1

A plant comprising a reactor, absorber, still condenser system and vaporizer as described for method A is employed. The distillation column is 1.37 m in diameter and 34 m high and comprises 45 sieve trays, 10 above the entry point for the aqueous formaldehyde solution fed from the first absorption stage of the absorber and 35 below. Within the column of 35 trays, there are 4 residence trays spaced at intervals of 7 sieve trays, each residence tray providing a 5 minute residence time. Per hour a gaseous mixture of 7,000 parts of methanol, 2,795 parts of water, 250 parts of formaldehyde and 11,032 parts of air is fed continuously to the reactor. Per hour an aqueous formaldehyde solution containing 5,622 parts of formaldehyde, 424 parts of methanol, 5,644 parts of water, 67 parts of nitrogen, 0.6 parts of hydrogen and 16.2 parts of carbon dioxide at a temperature of 70° C. is introduced continuously into the distillation column from the circulation loop of the first absorption stage of the absorber and passed downward in the distillation column. The temperature and pressure at the top and bottom of the distillation column are respectively 64° C. and 29 kPa and 86° C. and 63 kPa. The vapors emerging from the top of the distillation column comprise 764 parts of formaldehyde, 897 parts of methanol, 2,513 parts of water, and about 60 parts of nitrogen, 0.1 part of hydrogen and 16 parts of carbon dioxide. The vapors are passed to the reflux condenser at a pressure of 28 kPa. 2,910 parts of aqueous formaldehyde solution containing 18.3 wt. percent formaldehyde and 21.5 weight percent methanol is returned to the distillation column as reflux and the remainder of the condensate (1,358 parts) is combined with 20 parts of condensate from the vent condenser operated at a pressure of 27 kPa and recycled to the reactor. The recycled condensate comprises 250 parts of formaldehyde, 300 parts of methanol and 824 parts of water. 10,301 parts of aqueous formaldehyde solution containing 5,408 parts of formaldehyde, 117 parts of methanol and 4,776 parts of water is drawn off from the bottom of the stripping column as product. The yield is 82% and the conversion is 98.3%. The methanol content is 1.14 percent. The mol ratio of recycled methanol to recycled formaldehyde is 1.13. The net energy balance for the process is 320 megajoules per metric ton of product. When the distillation column is operated at about atmospheric pressure in the conventional rectification mode, the net energy required is increased to about 1,220 megajoules per metric ton of product.

EXAMPLE 2

A plant comprising a reactor, absorber, still condenser system and vaporizer as described for method B is employed. The distillation column comprises 35 sieve trays with 4 residence trays at intervals of 7 sieve trays, each residence tray providing a 5 minute residence time. Per hour a gaseous mixture of 7,001 parts of methanol, 2,795 parts of water, 255 parts of formaldehyde and 11,031 parts of air is fed continuously to the reactor. Per hour an aqueous formaldehyde solution containing 4,380 parts of formaldehyde, 156 parts of methanol and 3,038 parts of water at a temperature 86° C. is introduced continuously into the distillation column at a point at about 4 tenths of the height of the column, from the circulation loop of the first absorption stage of the absorber, and passed downward in the distillation column. Per hour an aqueous formaldehyde solution containing 2,733 parts of formaldehyde 371 parts of methanol and 4,542 parts of water at a temperature of 70° C. is drawn from the circulation loop of the second absorption stage and introduced continuously near the top of the distillation column and passed downward in the distillation column. Per hour 3,835 parts of an aqueous formaldehyde solution containing 1,437 parts of formaldehyde, 99 parts of methanol and 2,299 parts of water is taken from a point about half way up the distillation column and fed to the circulation loop of the first-absorption stage. The distillation column pressure and temperature are maintained at 29 kPa and 64° C. at the top of the column and 63 kPa and 86° C. at the bottom. The vapors emerging from the top of the distillation column comprise 674 parts of formaldehyde, 745 parts of methanol and 2,164 parts of water. The vapors are passed to the reflux condenser at a pressure of 28 kPa. 2,218 parts of aqueous formaldehyde solution containing 18.8 wt. percent formaldehyde and 20.8 weight percent methanol is returned to the distillation column as reflux and the remainder of the condensate (1,344 parts) is combined with 21 parts of condensate from the vent condenser operated at a pressure of 27 kPa, and recycled to the reactor. The recycled condensate comprises 255 parts of formaldehyde, 288 parts of methanol and 819 parts of water, 10,010 parts of aqueous formaldehyde solution containing 54.2 weight percent formaldehyde, 1.3 weight percent methanol and 44.5 weight percent water is drawn off from the bottom of the stripping column as product. The yield is 82% and the conversion is 98.3%. The mol ratio of recycled methanol to recycled formaldehyde is 1.06. The net energy balance for the process is 330 megajoules per metric ton of product. When the distillation column is operated at about atmospheric pressure in the conventional rectification mode, the net energy balance for the process is 1,230 megajoules per metric ton of product.

What is claimed is:

1. A process for the manufacture of an aqueous solution of formaldehyde comprising the steps of:
   (a) oxidatively dehydrogenating methanol with air in the presence of a silver or copper catalyst and steam at elevated temperature in a dehydrogenation reactor;
   (b) absorbing the reaction product in an absorption train comprising one or more absorption stages in series to form an aqueous formaldehyde solution containing free and combined method;
   (c) feeding the aqueous formaldehyde solution from the absorption train to a distillation column comprising at least about 1.5 theoretical plates for methanol stripping;
   (d) stripping a mixture of vapors of methanol, formaldehyde and water from the aqeuous formaldehyde solution by fractional distillation in the column at a pressure in the range of about 10 to about 105 kPa at the top of the column, wherein the concentration of water and methanol in the vapor mixture stripped from the column is greater than the concentration of water and methanol in the solution fed from the absorption train;
   (e) passing at least about 17 percent of the vapor mixture stripped from the column to the dehydrogenation reactor and returning the remainder as reflux to the distillation column; and
   (f) removing as product from the bottom of the stripping column as aqueous solution of formaldehyde containing a higher concentration of formaldehyde and a lower concentration of water and methanol than the solution fed to the column from the absorption train.

2. The process of claim 1 wherein the still column comprises at least about three theoretical plates.

3. The process of claim 1 or 2 wherein the height of the theoretical plate is in the range of about 0.5 to about 10 meters.

4. The process of claim 3 wherein the distillation column contains residence zones for the aqueous formaldehyde solution to permit a flow ratio of vapor to liquid in the column in the range of about 0.3 to about 1.5 by weight.

5. The process of claim 4 wherein the residence zones are chimney trays.

6. The process of claim 4 wherein the residence zones are circulation side loops and reservoirs.

7. The process of claim 4 wherein the pressure at the top of the distillation column is in the range of about 10 to about 50 kPa.

8. The process of claim 4 wherein the pressure at the top of the distillation column is in the range of about 20 to about 35 kPa.

9. The process of claim 8 wherein the temperature at the top of the distillation column is in the range of about 60° to about 85° C.

10. The process of claim 3 wherein the absorption train comprises two or more absorption stages, wherein portions of the circulating aqueous formaldehyde stream drawn from the bottom of at least the first two absorption stages are passed as separate streams to the column with the more dilute formaldehyde streams entering near the top and the more concentrated formaldehyde streams entering near the bottom of the column to provide a concentration gradient within the column and wherein a portion of each of the more dilute formaldehyde streams descending the column is drawn off as a side stream before it reaches the prior more concentrated formaldehyde solution entering the column and is added to the prior more concentrated aqueous formaldehyde absorption stage.

11. The process of claim 4 wherein the mol ratio of recycled methanol to recycled formaldehyde is at least 0.6.

12. The process of claim 4 wherein the mol ratio of recycled methanol to recycled formaldehyde is at least about 1.0.

13. The process of claim 4 wherein the mol ratio of recycled formaldehyde to total methanol fed to the reactor is less than about 0.035.

14. The process of claim 4 wherein the mixture of methanol, water and formaldehyde vapors emerging from the distillation column returned to the dehydrogenation reactor to the mixture refluxed to the column is in the ratio of 1:2.5 or less.

15. The process of claim 8 wherein the mixture of methanol, water and formaldehyde vapors emerging from the distillation column returned to the dehydrogenation reactor to the mixture refluxed to the column is in the ratio of 1:2.5 or less.

16. The process of claim 3 wherein the distillation column contains residence zones for the aqueous formaldehyde solution to provide a residence time of at least about 20 minutes.

17. The process of claim 16 wherein the residence zones are chimney trays.

18. The process of claim 16 wherein the residence zones are circulation side loops and reservoirs.

19. The process of claim 16 wherein the mixture of methanol, water and formaldehyde vapors emerging from the distillation column returned to the dehydrogenation reactor to the mixture refluxed to the column is in the ratio of 1:2.5 or less.

* * * * *